United States Patent
Sitte et al.

(10) Patent No.: US 6,178,757 B1
(45) Date of Patent: Jan. 30, 2001

(54) COOLING CHAMBER TEMPERATURE CONTROL DEVICE

(75) Inventors: Hellmuth Sitte, Seefeld (AT); Klaus Neumann, Bexbach-Saar; Helmut Haessig, Homburg-Saar, both of (DE)

(73) Assignee: Leica Microsysteme AG, Vienna (AT)

( * ) Notice: Under 35 U.S.C. 154(b), the term of this patent shall be extended for 0 days.

(21) Appl. No.: 09/387,559

(22) Filed: Sep. 1, 1999

(30) Foreign Application Priority Data

Sep. 1, 1998 (AT) .......................................... 1481

(51) Int. Cl.[7] .................................................. G01N 1/06
(52) U.S. Cl. ............................ 62/126; 62/51.1; 62/320; 165/263; 165/206; 83/915.5
(58) Field of Search ...................... 62/125, 126, 127, 62/129, 130, 173, 203, 320, 51.1; 165/263, 264, 206; 83/170, 171, 915.5

(56) References Cited

U.S. PATENT DOCUMENTS

| | | | |
|---|---|---|---|
| 4,314,459 | * | 2/1982 | Rivoire ............................ 165/263 X |
| 5,070,935 | * | 12/1991 | Sitte et al. ......................... 62/320 X |
| 5,960,640 | * | 10/1999 | Teppke ................................. 62/320 |
| 5,974,811 | * | 11/1999 | Heid et al. ...................... 83/915.5 X |

OTHER PUBLICATIONS

Sitte, Hellmuth, "Work Aid of the Technical/Scientific Periodical MTA–Journal with a General View/Summary of the Complete Field of Ultramicrotomy", Extra No. 10, pp. 1–33, 1985.

H. Sitte and K. Neumann, "Ultramicrotomes (Design—function—accessories)" Paper No. 1.1.2 in *Methods of Electron Microscopy* with English Summaries, Wissenschaftliche mbmbH, Verlagsgesellschaft mbH, pp. 1–248, Stuttgart, 1983.

* cited by examiner

Primary Examiner—Harry B. Tanner
(74) Attorney, Agent, or Firm—Foley & Lardner

(57) ABSTRACT

A device for controlling the temperatures in a cooling chamber for a microtome, in particular an ultramicrotome, comprises at least two different temperature control circuits for controlling the temperatures of the specimen and of the cutter. The control circuit for the temperature of the specimen (8) and the control circuit for the temperature of the cutter (9), as well as, if appropriate, the control circuit for the temperature of the chamber gas, have a common setting element (17), such that the control circuit can be programmed to an identical temperature as the set value.

16 Claims, 1 Drawing Sheet

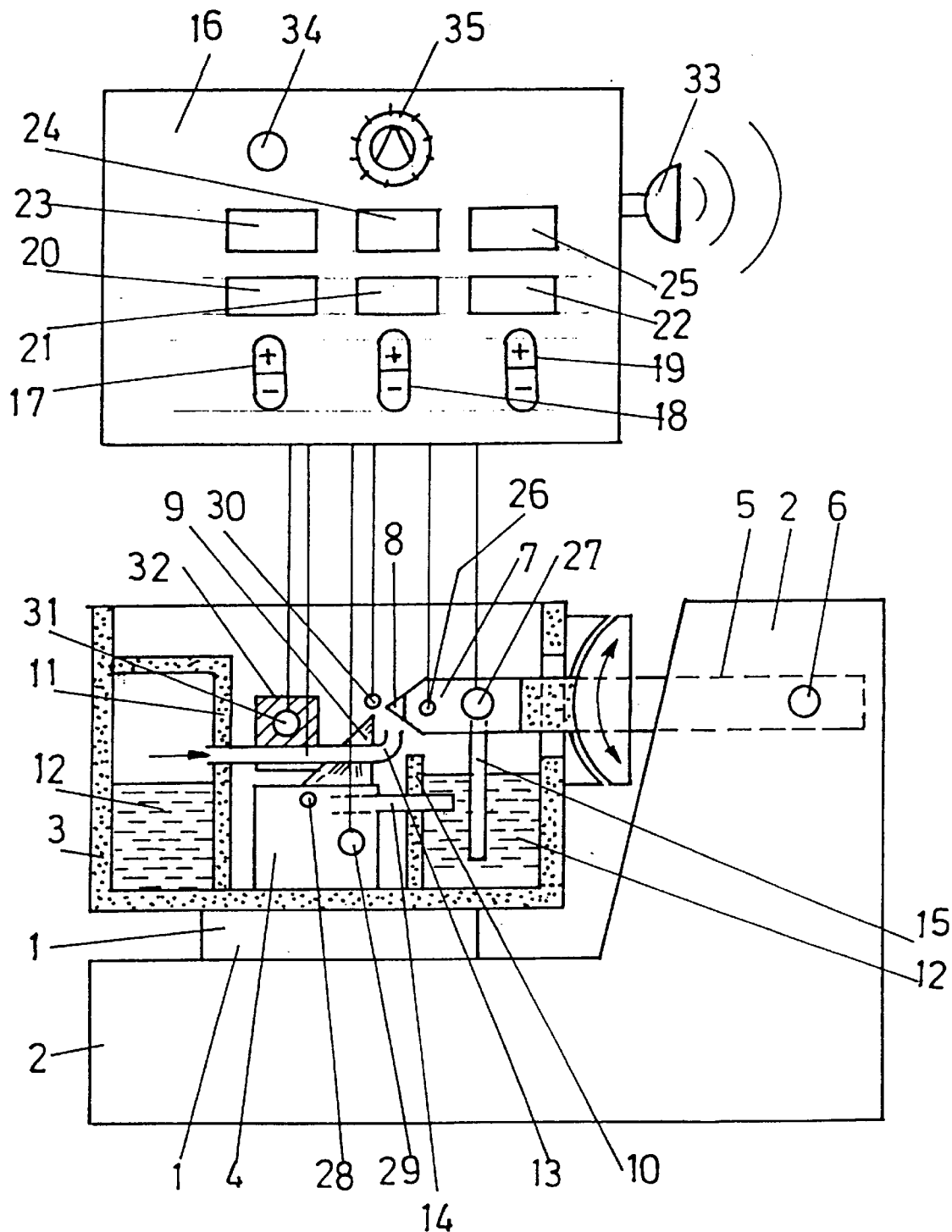

COOLING CHAMBER TEMPERATURE CONTROL DEVICE

BACKGROUND OF THE INVENTION

1. Field of the Invention

The invention relates to a device for controlling the temperatures in a cooling chamber for microtomes, in particular ultramicrotomes, having at least two different temperature control circuits for controlling the temperatures of the specimen and of the cutter.

2. Related Prior Art

The cutting of soft, elastic or hard samples, or, in very general terms, of materials whose consistency does not allow them to be cut at room temperature (e.g. aqueous suspensions, paints) requires cooling to temperatures which in some cases are well below room temperature. In this case, special cooling chambers are used for the microscopic, in particular electron-microscopic examination, and these cooling chambers, combined with suitable microtomes or ultramicrotomes, make it possible to remove sufficiently thin sections (cf. in this respect, inter alia, H. Sitte, Ultramikrotomie, in: mta-journal extra No. 10, Umschau-Verlag, Breidenstein GmbH, Frankfurt-Main, 1983). The temperature range of cooling chambers of this nature is between room temperature and approximately –180° C., and it is possible to control the temperatures of the specimen and of the cutter, and in many cases also of the chamber gas, separately. This separate control of the three important temperatures has long proven advantageous, since in this way it has been possible for all the thermal parameters which influence the cutting operation to be optimized separately. The cooling medium ("cryogen") used was in most cases either cold nitrogen gas ($N_{2g}$) from a Dewar vessel filled with liquid nitrogen ($N_{2l}$) or $N_{2l}$ for direct cooling. The gas which is present in the cooling chamber and floats around the cutter and specimen in these cases consists of pure $N_{2g}$.

The preselected temperatures of specimen, cutter and chamber gas were reached and kept constant in a technically known way using electronic control circuits which each have a temperature sensor (e.g. Pt 100 platinum resistor or microthermocouple) and a heater element (e.g. heating resistor). Setting elements allowed the desired temperatures to be preselected, and temperature indicators allowed the values reached in each case to be checked. If one takes into account the fact that the cutter temperature is the decisive factor for, for example, the use of certain float liquids (e.g. DMSO/$H_2O$), whereas the specimen temperature determines the consistency of the specimen (e.g. brittle or ductile, or liquid or solid), it will be understood that this type of separate temperature control of the three essential temperatures has without exception been felt to be optimum, and that cooling chambers of a very wide variety of designs and manufacturers were always equipped with the separate temperature control for specimen and cutter, and sometimes also for the chamber gas, which has been described.

In everyday practice, however, this principle exhibits considerable drawbacks and shortcomings which stem from the technical options available for precise temperature measurement in extremely small areas. Currently, it is technically impossible to measure the significant temperatures correctly. Even the smallest temperature sensors which operate virtually without inertia (e.g. microthermocouples) cannot be integrated in the outermost surface layers of the specimen. The specimen temperature always has to be measured at a lower layer which is, for example, at a distance of from 0.5 to 1 mm from the surface of the specimen and therefore from the location of the cutting process. The same applies to the cutting edge. It is not possible to arrange sensors at the actual cutting edge either in the diamond cutters which are preferably used nowadays in ultramicrotomy or in the less expensive metal or glass blades.

For practical reasons, the tendency is to position these sensors in the compact metal holders of the specimen and cutter in order to allow cutter and specimen to be replaced frequently in a simple and rapid manner. In many cases, the sensors arranged on these components show temperature values which are far removed from reality. This makes it almost impossible to reproduce the temperatures, particularly if cooling chambers of different designs or from different manufacturers are used.

The situation becomes particularly problematical if different temperatures are preselected for the specimen, cutter and chamber gas. It is known that a cold chamber gas cools the surfaces of cutter and specimen to well below the preselected or indicated values. Conversely, the thermal radiation from the warmer cutter onto the cooler specimen brings about significant warming of the surface layers of the specimen. It is scarcely possible to state the extent to which the indicated temperatures are a distortion of the true temperatures, and there is always a state of considerable uncertainty. This uncertainty is compounded by the dynamic phenomena which it is necessary to expect in view of the equilibria of flow, which often establish themselves slowly. Finally, attempting to achieve optimum results by systematically changing the three said temperatures is virtually pointless in practice, since the combination of equipment allows a virtually endless number of combinations. In any case, once an optimum temperature combination has been determined, this cannot readily be transferred to other cooling chambers, and in most cases is therefore of only very low systematic value.

Apart from these essential problems, it is necessary to carry out two, usually three or in special cases even more setting operations in order to preselect the temperatures which are desired in each case. Also, it is necessary to be convinced that all the preselected values have actually been reached before the sectioning is started after the temperature has been preselected or changed or before the sectioning is continued after the values have recently been changed. All in all, the result is a not insignificant delay in practical work for the majority of sectioning processes at reduced temperature.

SUMMARY OF THE INVENTION

In view of the foregoing, it is therefore an object of the invention to provide a more straightforward temperature control which in everyday use provides reproducible results even when cooling chambers of different designs and from different manufacturers are used.

According to one embodiment of the invention, this object can be achieved by implementing a control circuit for the temperature of the specimen and a control circuit for the temperature of the cutter having a common setting element, in that the control circuit can be programmed to a substantially identical temperature as the set value.

According to a further embodiment of the present invention, additional control circuits which are provided for the operation of the cooling chamber, for example for the chamber gas located in the chamber, in particular in the specimen-cutter area, can be incorporated in the common temperature pre-selection carried out using the setting element. In this way, all the relevant control circuits are programmed to the same temperature by a common control element—for example by the controller for the specimen temperature, which is the most important temperature. As a result, the control circuits, which according to the prior art are separate, set each of the temperatures to the same value, which consequently is reached within a very short time. Apart from the fact that this simplifies setting, it is also possible to achieve a very high reproducibility of the values irrespective of the particular design of the cooling chamber used and its principal components, since similar temperatures of the various components automatically rule out the possibility of heating or cooling effects caused by components of the cooling chamber being at different temperatures.

Further features of the invention form the subject matter of the claims and will be explained in more detail, in conjunction with further advantages of the invention, with reference to exemplary embodiments.

BRIEF DESCRIPTION OF THE DRAWINGS

An embodiment of the invention, serving as an example, is illustrated schematically in the drawings, in which:

FIG. 1 shows a schematic diagram of a cooling chamber attached to a microtome/ultramicrotome, together with the control panel of the control unit of the present invention.

DETAILED DESCRIPTION OF THE EXEMPLARY EMBODIMENTS

The microtome/ultramicrotome illustrated in FIG. 1 is similar in several respects to a conventional design (cf. in this respect also H. Sitte, 1983, l.c., and H. Sitte and K. Neumann, Ultramikrotome und apparative Hilfsmittel der Ultramikrotomie [Ultramicrotomes and auxiliary apparatus for ultramicrotomy], in: G. Schimmel and W. Vogell, Methodensammlung der Elektronenmikroskopie [Collection of methods used in electron microscopy], Wissenschaftliche Verlags-GmbH, Stuttgart 1983).

As shown in FIG. 1, a cooling chamber 3 is attached to a cutter support 1 of a microtome/ultramicrotome 2. A cutter holder 4 is mounted at the bottom of the cooling chamber 3. A specimen-carrier bar 5 is introduced through the rear wall of the cooling chamber 3 and executes an oscillating up-and-down movement about a bearing 6 during the sectioning. A specimen holder 7 with a specimen 8 is attached to the free end of the bar 5 and, in the course of the cutting movement (double arrow) is guided past the cutting edge of a cutter 9.

Interconnected tanks are filled from the outside with $N_{2l}$ (liquid nitrogen) 12, from which $N_{2g}$ (gaseous nitrogen) evaporates into the chamber. Some of this $N_{2g}$ is guided through a tube 13 into the specimen-cutter area. The cutter holder 4 is thermally connected to the $N_{2l}$ 12 in the tank section 10 by metal bar 14, and specimen holder 7 is thermally connected to the $N_{2l}$ 12 in the tank section 10 by the metal section 15.

According to the invention, the temperature control is effected by the electronics of the control unit 16, on the control panel of which, by way of example, there are three rocker switches 17/18/19 for setting the temperature, and three digital indicators 20/21/22 for indicating the actual values or 23/24/25 the preselected set values for specimen, cutter and $N_{2g}$. The control unit 16 further includes a microcontroller, such as a conventional microprocessor (not shown), that can be used to facilitate the control circuit(s). In addition, a temperature sensor 26 and a heating resistor 27 for controlling and indicating the temperature are arranged in the specimen holder 7. Similar elements 28/29 are located in the cutter holder 4. Directly next to the cutting edge of the cutter 9, free inside the chamber gas, there is the sensor 30 for the $N_{2g}$ temperature, which can be varied by the heater element 31 in the metal block 32 which surrounds the tube 13.

In such a device, the invention can be realized by using suitable software for the microcontroller, in a technically known way, to carry out the temperature preselection at least for the specimen temperature and cutter temperature, and if appropriate also for the $N_{2g}$ temperature, by actuating only the setting element 17 for the specimen. The set value indicators 23/24/25 then show identical values (e.g. −90° C.) for all three control circuits, and the actual value indicators 20/21/22 seek to reach this uniform desired value. For example, a voltage proportional to the temperature can be used as a control parameter for the control circuit, where the voltage is determined by the temperature sensor.

Another embodiment of the invention comprises an acoustic and/or optical signal indicator, which responds when at least specimen and cutter, and preferably also the chamber gas, have at least approximately reached the preselected common set temperature value. This signal indicator therefore indicates the readiness of the device, i.e. the fact that an equilibrium state ("steady state") has been reached. This means that, for example for a preselected temperature of −90° C. for the specimen, a signal indicates that the preselected and desired state has been reached when specimen, cutter and chamber gas have approximately reached this temperature.

For example, the device shown in FIG. 1 may further include an optical and/or acoustic signal indicator, for example a buzzer 33 arranged in the control unit 16 or an indicator light (e.g. LED) 34 arranged on the control panel of the control unit 16. The indicator is used to indicate that the desired values of the identically set control circuits for the specimen, the cutter and, if appropriate, the $N_{2g}$ temperature has been reached, with an acoustic or optical signal. A suitable design may also comprise a combination of both signals, e.g. a brief signal from the buzzer 33 combined with simultaneous prolonged illumination of an indicator light 34.

A further configuration of the invention includes controlled, variable establishment of the tolerance limits for reaching the set values. While in the previous example a signal indicating that the set values have been reached is only indicated, for example, when the actual values correspond to the desired values to within the measurement accuracy of the system, it is in this case advantageously possible for the signal which indicates that the system is ready to cut to be triggered as soon as the actual values have approached the set values to within a tolerance limit which can be preselected. This tolerance limit may, for example, be set to values of between +/−1 and +/−10° C., using an analog rotary button 34 arranged on the control panel of the control unit 16, and can thus be adapted to the specific requirements of the particular sectioning operation.

The system according to the invention may be realized with suitable adaptation to the different designs of cooling chambers for standard microtomes or ultramicrotomes and to the different requirement in specific working areas in various combinations and with various structural elements. This applies in particular to the design of the control circuits and the digital or analog indicators and setting devices used for these circuits. In particular, the accuracy of settings and indicators are not significant and are essentially to be aligned according to practical requirements. It is also insignificant whether the system according to the invention, in the case of relatively simple cooling chambers, is produced on its own, i.e., without the possibility of separate, different setting of the specimen temperature and cutter temperature, and also the extent to which other temperature-control circuits, such as for example that for controlling the $N_{2g}$ temperature or for a cutting press, are incorporated in the overall system.

A further embodiment of the invention includes an acoustic and/or optical signal indicator, such as those described above, that also responds when the actual values of the individual temperatures deviate from the common set value by amounts which are less than the tolerance range which has been preselected with a setting element. In this way, it is possible, for example, when working with specimens which are relatively insensitive and whose cutting consistency scarcely changes within a range of +/−5° C., to input this range to the electronic unit in a technically known way by means of an analog or digital setting element and, in this way, to reach the signal which allows sectioning more quickly than with a more critical specimen for which it is necessary to use and preselect a tolerance width of, for example, +/−1° C.

The common setting element according to the invention for setting an identical set value for the temperature of a plurality of control circuits may be the only temperature-setting element of the device. However, it is also possible for the device to have separate setting elements for individual control circuits, in order—if in a specific case a uniform temperature selection for all the control circuits is unsuitable—for it to be possible to separately control the temperatures of the individual control circuits (as is known per se). For example, next to the setting element for the specimen temperature, which may also be the common setting element for both the specimen temperature and the cutter temperature (and, if appropriate, the chamber-gas temperature), there may also be an additional setting element for the cutter temperature (and, if appropriate, for the chamber-gas temperature). It is then strightforward, when required, to desist from using uniform temperatures by actuating the setting elements for the cutter temperature and/or the chamber-gas temperature after the specimen temperature has been preselected, and, in this way, deactivating the uniform control. In this way, the more complex individual control which has hitherto been customary is deliberately restored for specific individual situations, making the system universally usable despite the possible simplification.

Although the invention has been described above by reference to certain embodiments of the invention, the invention is not limited to the embodiments described above. Modifications and variations of the embodiments described above will occur to those skilled in the art, in light of the above teachings. The scope of the invention is defined with reference to the following claims.

Austrian Patent Application No. A 1481/98 filed Sep. 1, 1998, including the specification, the drawings, the claims, and the abstract, upon which this application is based, is incorporated herein by reference in its entirety.

What is claimed is:

1. A device for controlling the temperatures in a cooling chamber for a microtome, comprising:
   a control unit for providing an indication of temperatures in the microtome and for indicating a set value, said control unit including a microcontroller having a first temperature control circuit for controlling a temperature of a specimen disposed in the microtome and a second temperature control circuit for controlling a temperature of a cutter of the microtome; and
   a setting element common to said first and second control circuits, wherein said first and second control circuits are capable of being programmed to a substantially identical temperature as said set value.

2. The device according to claim 1, wherein said microtome is an ultramicrotome.

3. The device according to claim 1, said microcontroller further comprising:
   a third control circuit for controlling the temperature of the cooling chamber.

4. The device according to claim 3, wherein a temperature of a chamber gas located in an area proximate to said specimen and said cutter is pre-selected using said setting element.

5. The device according to claim 3, wherein said control unit further comprises:
   an indicator for providing an indication when at least said specimen and said cutter have at least approximately reached a pre-selected common set temperature value.

6. The device of claim 5, wherein said indicator is selected from the group consisting of acoustic and optical signal indicators.

7. The device according to claim 5, wherein said indicator provides an indication when actual values of individual temperatures of said specimen, cutter, and cooling chamber deviate from a common set value by an amount less than a pre-selected tolerance range that is set with a second setting element coupled to said control unit.

8. The device according to claim 3, comprising:
   first, second, and third setting elements, each coupled to said control unit, for separate pre-selection of temperatures of said first, second, and third control circuits.

9. A method of controlling one or more temperatures in a cooling chamber for a microtome, comprising:
   controlling a temperature of a specimen disposed in the microtome;
   controlling a temperature of a cutter of the microtome; and
   pre-selecting a set value temperature of the specimen and the cutter with a common setting element such that the temperatures of the specimen and the cutter are capable of reaching a substantially identical temperature as said set value.

10. The method according to claim 9, further comprising:
    controlling a temperature of a chamber gas of the cooling chamber; and
    pre-selecting a set value temperature of the chamber gas such that the temperatures of the specimen, chamber gas, and cutter are capable of reaching a substantially identical temperature as the set value.

11. The method according to claim 10, further comprising:
    providing an indication when actual values of individual temperatures of the specimen, cutter, and chamber gas deviate from the set value by an amount less than a pre-selected tolerance range.

12. A device for controlling the temperatures in a cooling chamber for a microtome, in particular an ultramicrotome, having at least two different temperature control circuits for controlling the temperatures of the specimen and of the cutter, wherein (at least) the control circuit for the temperature of the specimen (8) and the control circuit for the temperature of the cutter (9) have a common setting element (17), by means of which the control circuit can be programmed to an identical temperature as the set value.

13. The device according to claim 12, wherein further control circuits which are provided for the operation of the cooling chamber, for example for the chamber gas located in the chamber, in particular in the specimen-cutter area, are incorporated in the common temperature pre-selection carried out using the setting element (17).

14. The device according to claim 12, wherein an acoustic (33) and/or optical (34) signal indicator is provided, which responds when at least specimen and cutter, and preferably also the chamber gas, have at least approximately reached the pre-selected common set temperature value (23).

15. The device according to claim 14, wherein the acoustic (33) and/or optical (34) signal indicator also responds when the actual values of the individual temperatures (20, 21, 22) deviate from the common set value (23) by amounts which are less than the tolerance range which has been pre-selected by means of a setting element (35).

16. The device according to claim 12, wherein setting elements (17, 18, 19) for the optional separate pre-selection of the temperatures of the individual control circuits are also provided.

* * * * *